US 8,592,473 B2

(12) United States Patent
Reid

(10) Patent No.: US 8,592,473 B2
(45) Date of Patent: *Nov. 26, 2013

(54) TRIAZOL COMPOUNDS FOR TREATING BIOFILM FORMATION

(75) Inventor: David Reid, Hobart (AU)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/606,550

(22) Filed: Sep. 7, 2012

(65) Prior Publication Data

US 2012/0329746 A1 Dec. 27, 2012

Related U.S. Application Data

(63) Continuation of application No. 12/600,667, filed as application No. PCT/EP2008/056231 on May 21, 2008.

(30) Foreign Application Priority Data

May 22, 2007 (EP) .................... 07108650

(51) Int. Cl.
*A61K 31/41* (2006.01)
(52) U.S. Cl.
USPC ........................................ 514/383
(58) Field of Classification Search
None
See application file for complete search history.

(56) References Cited

U.S. PATENT DOCUMENTS

| 5,462,644 | A | * | 10/1995 | Woodson | ........................ 205/701 |
| 6,465,504 | B1 | | 10/2002 | Lattmann et al. | |
| 6,596,750 | B2 | | 7/2003 | Lattmann et al. | |
| 6,759,040 | B1 | * | 7/2004 | Manyak et al. | ............... 424/94.2 |
| 7,074,815 | B2 | | 7/2006 | Lattmann et al. | |
| 8,309,590 | B2 | * | 11/2012 | Reid | ............................ 514/383 |
| 2003/0069273 | A1 | | 4/2003 | Lattmann et al. | |
| 2003/0073611 | A1 | * | 4/2003 | Gudkov et al. | ................... 514/1 |

FOREIGN PATENT DOCUMENTS

| JP | 2003527417 A | 9/2003 |
| JP | 2005525849 A | 9/2005 |
| JP | 2006512290 A | 4/2006 |
| WO | 0170213 A2 | 9/2001 |
| WO | 03075654 A2 | 9/2003 |
| WO | 2004016213 A2 | 2/2004 |
| WO | 2004035026 A1 | 4/2004 |

OTHER PUBLICATIONS

Weinberg. Suppression of bacterial biofilm formation by iron limitation. Medical Hypotheses, 2004, Vo. 63, pp. 863-865.*
Weinberg E.D.: "Supression of bacterial biofilm formation by iron limitation", Medical Hypothses, EDEN Press, Penrith, US, vol. 63, No. 5, 2004, pp. 863-865.
Singh Pradeep K et al: "A component of innate immunity prevent bacterial biofilm development", Nature May 30, 2002, vol. 417, No. 6888, pp. 552-555.
Lewis K.: "Riddle of biofilm resistance", Antimicrobial Agents and Chemotherapy, American Society for Microbiology, Washington, DC, US, vol. 45, No. 4 Apr. 2001, p. 1005.
Reed Catilin et al: "Deferasirox, an iron-chelating agent, as salvage therapy for rhinocerebral mucormycosis", Antimicrobial Agents and Chemotherapy, Nov. 2006, vol. 50, No. 11, pp. 3968-3969.
Moreau-Marquis S et al., Tobramycin and FDA-approved iron chelators eliminate *Pseudomonas aeruginosa* biofilms on cystic fibrosis cells, Am J Respir Cell Mol Biol. Sep. 2009 41(3): 305-13.
Singh Pradeep K et al "Quorum-sensing signals indicate that cystic fibrosis lungs are infected with bacterial biofilms" Nature 407:762-764 2000.

* cited by examiner

*Primary Examiner* — Marcela M Cordero Garcia
(74) *Attorney, Agent, or Firm* — Lisa Matovcik

(57) ABSTRACT

The present invention relates to the use of a Compound of formula I, (I)

Figure 1:
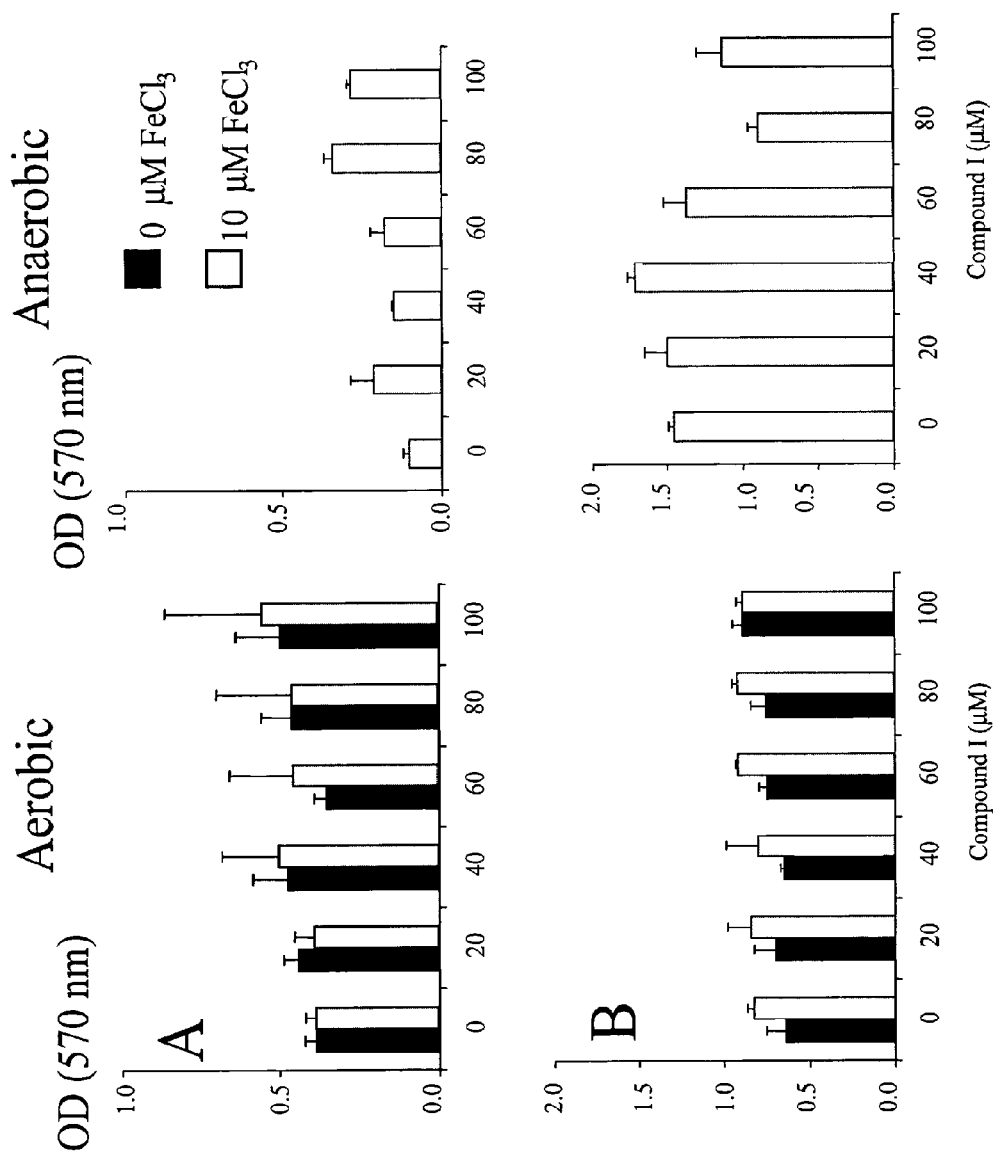

[Chemical structure of formula I showing triazole with two phenyl substituents bearing R1, R2, R3, R4, R5 groups]

preferably 4-[3,5-bis(2-hydroxyphenyl)-[1,2,4]triazol-1-yl] benzoic acid or a pharmaceutically acceptable salt thereof for the preparation of a medicament for use in the treatment of biofilm formation, e.g. of *P. aeruginosa*, e.g. in cystic fibrosis patients.

16 Claims, 5 Drawing Sheets

TRIAZOL COMPOUNDS FOR TREATING BIOFILM FORMATION

The present invention relates to the use of Compound of formula 4-[3,5-Bis-(2-hydroxyphenyl)-[1,2,4]-triazol-1-yl] benzoic acid (Compound of formula I) to inhibit or disrupt the formation of biofilms by the bacterium *Pseudomonas aeruginosa* under the sorts of environment conditions encountered in the lungs of individuals suffering from the lethal genetic disorder, Cystic fibrosis.

Cystic fibrosis is one of the most common life-shortening, childhood-onset inherited diseases. In the United States, incidence is 1 in 1000. In Victoria, Australia, incidence is 1 in 3600. In northern Italy, incidence is 1 in 4300. It is most common among Europeans and Ashkenazi Jews; one in twenty-two people of European descent carry one gene for CF, making it the most common genetic disease among them.

Cystic fibrosis, abbreviated as CF, also called mucoviscidosis, is an hereditary disease that affects the entire body, causing progressive disability and early death. Formerly known as cystic fibrosis of the pancreas, this entity has increasingly been labeled simply 'cystic fibrosis'. CF is caused by a mutation in a gene called the cystic fibrosis transmembrane conductance regulator (CFTR). The product of this gene helps create sweat, digestive juices, and mucus. Although most people without CF have two working copies of the CFTR gene, only one is needed to prevent cystic fibrosis. CF develops when neither gene works normally. Therefore, CF is considered an autosomal recessive disease. The name cystic fibrosis refers to the characteristic 'fibrosis' (tissue scarring) and cyst formation within the pancreas, first recognized in the 1930s. Difficult breathing and insufficient enzyme production in the pancreas are the most common symptoms. Thick mucous production as well as a low immune system results in frequent lung infections, which are treated, though not always cured, by oral and intravenous antibiotics and other medications.

The lungs of individuals with cystic fibrosis are colonized and infected by bacteria from an early age. These bacteria, which often spread amongst individuals with CF, thrive in the altered mucus, which collects in the small airways of the lungs. This mucus encourages the development of bacterial microenvironments, e.g. biofilms, that are difficult for immune cells and antibiotics to penetrate. The lungs respond to repeated damage by thick secretions and chronic infections by gradually remodeling the lower airways, e.g. bronchiectasis, making infection even more difficult to eliminate. Over time, both the types of bacteria and their individual characteristics change in individuals with CF. Initially, common bacteria such as *Staphylococcus aureus* and *Hemophilus influenzae* colonize and infect the lungs. Eventually, however, *Pseudomonas aeruginosa* and sometimes *Burkholderia cepacia* dominates. Once within the lungs, these bacteria adapt to the environment and develop resistance to commonly used antibiotics. *Pseudomonas* can develop special characteristics which allows the formation of large colonies—these strains are known as "mucoid" *Pseudomonas* and are rarely seen in people who do not have cystic fibrosis.

A biofilm is an aggregate of microbes with a distinct architecture. A biofilm is like a tiny city in which microbial cells, each only a micrometer or two long, form towers that can be hundreds of micrometers high. The "streets" between the towers are really fluid-filled channels that bring in nutrients, oxygen and other necessities for live biofilm communities.

Biofilms form on the surface of catheter lines and contact lenses. They grow on pacemakers, heart valve replacements, artificial joints and other surgical implants. The CDC (Centers for Disease Control) estimate that over 65% of nosocomial (hospital-acquired) infections are caused by biofilms.

Bacteria growing in a biofilm are highly resistant to antibiotics, up to 1,000 times more resistant than the same bacteria not growing in a biofilm. Standard antibiotic therapy is often useless and the only recourse may be to remove the contaminated implant.

*Pseudomonas aeruginosa* is a Gram-negative, aerobic, rod-shaped bacterium with unipolar motility. An opportunistic human pathogen, *P. aeruginosa* is also an opportunistic pathogen of plants.

*P. aeruginosa* is naturally resistant to a large range of antibiotics and may demonstrate additional resistance after unsuccessful treatment, particularly through modification of a porin. It should usually be possible to guide treatment according to laboratory sensitivities, rather than choosing an antibiotic empirically. If antibiotics are started empirically, then every effort should be made to obtain cultures and the choice of antibiotic used should be reviewed when the culture results are available.

Antibiotics that have activity against *P. aeruginosa* include aminoglycosides, e.g. gentamicin, amikacin, tobramycin, quinolones, e.g. ciprofloxacin, and levofloxacin; cephalosporins, e.g. ceftazidime, cefepime, cefpirome; ureidopenicillines such as piperacillin, ticarcillin; carbapenems, such as meropenem, imipenem; polymyxins such as polymyxin B, colistin and monobactams, such as for example aztreonam.

The bacterium *Pseudomonas aeruginosa* is a versatile and problematical pathogen in human disease. In the respiratory tract it causes both community acquired and nocosomial pneumonia, the latter being associated with a high mortality in patients with briochiectasis and is the predominant pathogen in patient suffering from the genetic disorder cystic fibrosis, abbreviated as CF. It also causes infection in burns and ischaemic wounds and frequently contaminates medical devices. Many *P. aeruginosa* infections are resistant to conventional therapy, i.e. antibiotics because the organism can adopt a biofilm existence. In CF, for example, *P. aeruginosa* grow as exopolysaccharide embedded microcolonies within the lung mucous. Under these conditions, resistance to antibiotics is enhanced by factors such as locally lowered oxygen tension due to slow diffusion through the biofilm. Together these factors make *P. aeruginosa* in chronic biofilm-associated infections almost impossible to treat.

New strategies are therefore needed to treat chronic *P. aeruginosa* infections and to eliminate biofilms, e.g. of *P. aeruginosa*, e.g. in CF patients.

Compounds of formula I, e.g. Compound I, can be used to eliminate biofilms, e.g. biofilm formation of *P. aeruginosa*, e.g. in cystic fibrosis patients, and/or to treat the biofilm formation of *P. aeruginosa*, e.g. in CF patients.

Compounds of formula I as described below, and Compound I, i.e. 4-[3,5-Bis-(2-hydroxyphenyl)-[1,2,4]-triazol-1-yl]benzoic acid having the following formula

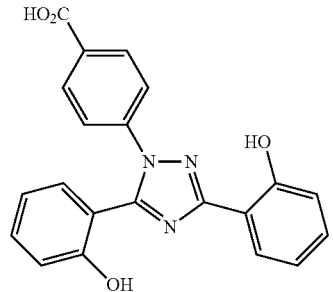

in the free acid form, salt thereof and its crystalline forms are disclosed in U.S. Pat. No. 6,465,504 B1.

In one aspect, the present invention relates thus to the use of an iron chelator of general formula I

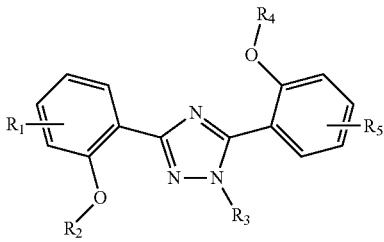

wherein
$R_1$ and $R_5$ simultaneously or independently of one another are hydrogen, halogen, hydroxyl, lower alkyl, halo-lower alkyl, lower alkoxy, halo-lower alkoxy, carboxyl, carbamoyl, N-lower alkylcarbamoyl, N,N-di-lower alkylcarbamoyl or nitrile;
$R_2$ and $R_4$ simultaneously or independently of one another are hydrogen, unsubstituted or substituted lower alkanoyl or aroyl, or a radical which can be removed under physiological conditions, e.g. a protective group;
$R_3$ is hydrogen, lower alkyl, hydroxy-lower alkyl, halo-lower alkyl, carboxy-lower alkyl, lower alkoxycarbonyl-lower alkyl, $R_6R_7N$—C(O)-lower alkyl, unsubstituted or substituted aryl or aryl-lower alkyl, or unsubstituted or substituted heteroaryl or heteroaralkyl;
$R_6$ and $R_7$ simultaneously or independently of one another are hydrogen, lower alkyl, hydroxy-lower alkyl, alkoxy-lower alkyl, hydroxyalkoxy-lower alkyl, amino-lower alkyl, N-lower alkylamino-lower alkyl, N,N-di-lower alkylamino-lower alkyl, N-(hydroxy-lower alkyl)amino-lower alkyl, N,N-di(hydroxy-lower alkyl)amino-lower alkyl or, together with the nitrogen atom to which they are bonded, form an azaalicyclic ring; or a pharmaceutically acceptable salt thereof; for the treatment of biofilm of P. aeruginosa.

Preferably, the invention relates to above described use comprising at least one compound of the formula (I), in which $R_1$ and $R_5$ simultaneously or independently of one another are hydrogen, halogen, hydroxyl, lower alkyl, halo-lower alkyl, lower alkoxy or halo-lower alkoxy; $R_2$ and $R_4$ simultaneously or independently of one another are hydrogen or a radical which can be removed under physiological conditions; $R_3$ is lower alkyl, hydroxy-lower alkyl, carboxy-lower alkyl, lower alkoxycarbonyl-lower alkyl, $R_6R_7N$—C(O)-lower alkyl, substituted aryl, aryl-lower alkyl, substituted by N-lower alkylamino, N,N-di-lower alkylamino or pyrrolidino, or unsubstituted or substituted heteroaryl or heteroaralkyl; $R_6$ and $R_7$ simultaneously or independently of one another are hydrogen, lower alkyl, hydroxy-lower alkyl, alkoxy-lower alkyl, hydroxyalkoxy-lower alkyl, amino-lower alkyl, N-lower alkylamino-lower alkyl, N,N-di-lower alkylamino-lower alkyl, N-(hydroxy-lower alkyl)amino-lower alkyl, N,N-di(hydroxy-lower alkyl)amino-lower alkyl or, together with the nitrogen atom to which they are bonded, form an azaalicyclic ring; and salts thereof; and at least one pharmaceutically acceptable carrier, and to methods for their preparation.

Preferably, within the above mentioned used the preferred compound of formula I is 4-[3,5-bis(2-hydroxyphenyl)-[1,2,4]triazol-1-yl]benzoic acid or a pharmaceutically acceptable salt.

The compounds of formula I can be prepared as described in e.g. U.S. Pat. No. 6,596,750 B2 or U.S. Pat. No. 6,465,504 B1 or EP 0914118.

Halogen is, for example, chlorine, bromine or fluorine, but can also be iodine.

The prefix "lower" designates a radical having not more than 7 and in particular not more than 4 carbon atoms.

Alkyl is straight-chain or branched. Per se, for example lower alkyl, or as a constituent of other groups, for example lower alkoxy, lower alkylamine, lower alkanoyl, lower alkylaminocarbonyl, it can be unsubstituted or substituted, for example by halogen, hydroxyl, lower alkoxy, trifluoromethyl, cyclo-lower alkyl, azaalicyclyl or phenyl, it is preferably unsubstituted or substituted by hydroxyl.

Lower alkyl is, for example, n-propyl, isopropyl, n-butyl, isobutyl, sec-butyl, tert-butyl, n-pentyl, neopentyl, n-hexyl or n-heptyl, preferably methyl, ethyl and n-propyl. Halo-lower alkyl is lower alkyl substituted by halogen, preferably chlorine or fluorine, in particular by up to three chlorine or fluorine atoms.

Lower alkoxy is, for example, n-propoxy, isopropoxy, n-butoxy, isobutoxy, sec-butoxy, tert-butoxy, n-amyloxy, isoamyloxy, preferably methoxy and ethoxy. Halo-lower alkoxy is lower alkoxy substituted by halogen, preferably chlorine or fluorine, in particular by up to three chlorine or fluorine atoms.

Carbamoyl is the radical $H_2N$—C(O)—, N-lower alkylcarbamoyl is lower alkyl-HN—C(O)— and N,N-di-lower alkylcarbamoyl is di-lower alkyl-N—C(O)—.

Lower alkanoyl is HC(O)— and lower alkyl-C(O)— and is, for example, acetyl, propanoyl, butanoyl or pivaloyl.

Lower alkoxycarbonyl designates the radical lower alkyl-O—C(O)— and is, for example, n-propoxycarbonyl, isopropoxycarbonyl, n-butoxycarbonyl, isobutoxycarbonyl, sec-butoxycarbonyl, tert-butoxycarbonyl, n-amyloxycarbonyl, isoamyloxycarbonyl, preferably methoxycarbonyl and ethoxycarbonyl.

Aryl, per se, for example aryl, or as a constituent of other groups, for example aryl-lower alkyl or aroyl, is, for example, phenyl or naphthyl, which is substituted or unsubstituted. Aryl is preferably phenyl which is unsubstituted or substituted by one or more, in particular one or two, substituents, for example lower alkyl, lower alkoxy, hydroxyl, nitro, halogen, trifluoromethyl, carboxyl, lower alkoxycarbonyl, amino, N-lower alkylamino, N,N-di-lower alkylamino, aminocarbonyl, lower alkylaminocarbonyl, di-lower alkylaminocarbonyl, heterocycloalkyl, heteroaryl or cyano. Primarily, aryl is unsubstituted phenyl or naphthyl, or phenyl which is substituted by lower alkyl, lower alkoxy, hydroxyl, halogen, carboxyl, lower alkoxycarbonyl, N,N-di-lower alkylamino or heterocycloalkylcarbonyl.

Aroyl is the radical aryl-C(O)— and is, for example, benzoyl, toluoyl, naphthoyl or p-methoxybenzoyl.

Aryl-lower alkyl is, for example, benzyl, p-chlorobenzyl, o-fluorobenzyl, phenylethyl, p-tolylmethyl, p-dimethylaminobenzyl, p-diethylaminobenzyl, p-cyanobenzyl, p-pyrrolidinobenzyl.

Heterocycloalkyl designates a cycloalkyl radical having 3 to 8, in particular having from 5 to not more than 7, ring atoms, of which at least one is a heteroatom; oxygen, nitrogen and sulfur are preferred. Azaalicyclyl is a saturated cycloalkyl radical having 3 to 8, in particular 5 to 7, ring atoms, in which at least one of the ring atoms is a nitrogen atom. Azaalicyclyl can also contain further ring heteroatoms, e.g. oxygen, nitrogen or sulfur; it is, for example, piperidinyl, piperazinyl, morpholinyl or pyrrolidinyl. Azaalicyclyl radicals can be unsubstituted or substituted by halogen or lower alkyl. The azaalicyclyl radicals bonded via a ring nitrogen atom, which are preferred, are, as is known, designated as piperidino, piperazino, morpholino, pyrrolidino etc.

Heteroaryl per se, for example heteroaryl, or as a constituent of other substituents, for example heteroaryl-lower alkyl, is an aromatic radical having from 3 to not more than 7, in particular from 5 to not more than 7, ring atoms, in which at least one of the ring atoms is a heteroatom, e.g. pyrrolyl, imidazolyl, triazolyl, tetrazolyl, oxazolyl, thiazolyl, furanyl, thiophenyl, pyridyl, pyrazinyl, oxazinyl, thiazinyl, pyranyl or pyrimidinyl. Heteroaryl can be substituted or unsubstituted. Heteroaryl which is unsubstituted or substituted by one or more, in particular one or two, substituents, for example lower alkyl, halogen, trifluoromethyl, carboxyl or lower alkoxycarbonyl, is preferred.

Heteroaryl-lower alkyl designates a lower alkyl radical in which at least one of the hydrogen atoms, preferably on the terminal C atom, is replaced by a heteroaryl group if the alkyl chain contains two or more carbon atoms.

N-lower alkylamino is, for example, n-propylamino, n-butylamino, i-propylamino, i-butylamino, hydroxyethylamino, preferably methylamino and ethylamino. In N,N-di-lower alkylamino, the alkyl substituents can be identical or different. Thus N,N-di-lower alkylamino is, for example, N,N-dimethylamino, N,N-diethylamino, N,N-methylethylamino, N-methyl-N-morpholinoethylamino, N-methyl-N-hydroxyethylamino or N-methyl-N-benzylamino.

Protective groups, their introduction and removal are described, e.g., in McOmie, Protective Groups in Organic Chemistry, Plenum Press, London, N.Y. (1973), and in Methoden der organischen Chemie [Methods of organic chemistry], Houben-Weyl, 4th Edition, Vol. 1571, Georg Thieme, Stuttgart (1974), and also in Greene, Protective Groups in Organic Synthesis, John Wiley, New York (1981). It is characteristic of protective groups that they can be removed easily, i.e. without undesired side reactions taking place, e.g. solvolytically, reductively, photolytically or alternatively under physiological conditions. Hydroxyl groups can be present, e.g., in the form of an easily cleavable ester or ether group, preferably of an alkanoyl or aralkanoyl ester group or of a cycloheteroalkyl, aralkyl or alkoxyalkyl ether group, but also of a silyl ester or silyl ether group, in particular as an acetyl or benzoyl ester or as a tetrahydropyranyl, benzyl or methoxymethyl ether.

Salts of compounds of the formula (I) are pharmaceutically acceptable salts, especially salts with bases, such as appropriate alkali metal or alkaline earth metal salts, e.g. sodium, potassium or magnesium salts, pharmaceutically acceptable transition metal salts such as zinc salts, or salts with organic amines, such as cyclic amines, such as mono-, di- or tri-lower alkylamines, such as hydroxy-lower alkylamines, e.g. mono-, di- or trihydroxy-lower alkylamines, hydroxy-lower alkyl-lower alkylamines or polyhydroxy-lower alkylamines. Cyclic amines are, for example, morpholine, thiomorpholine, piperidine or pyrrolidine. Suitable mono-lower alkylamines are, for example, ethyl- and tert-butylamine; di-lower alkylamines are, for example, diethyl- and diisopropylamine; and tri-lower alkylamines are, for example, trimethyl- and triethylamine. Appropriate hydroxy-lower alkylamines are, for example, mono-, di- and triethanolamine; hydroxy-lower alkyl-lower alkylamines are, for example, N,N-dimethylamino- and N,N-diethylaminoethanol; a suitable polyhydroxy-lower alkylamine is, for example, glucosamine. In other cases it is also possible to form acid addition salts, for example with strong inorganic acids, such as mineral acids, e.g. sulfuric acid, a phosphoric acid or a hydrohalic acid, with strong organic carboxylic acids, such as lower alkanecarboxylic acids, e.g. acetic acid, such as saturated or unsaturated dicarboxylic acids, e.g. malonic, maleic or fumaric acid, or such as hydroxycarboxylic acids, e.g. tartaric or citric acid, or with sulfonic acids, such as lower alkane- or substituted or unsubstituted benzenesulfonic acids, e.g. methane- or p-toluenesulfonic acid. Compounds of the formula (I) having an acidic group, e.g. carboxyl, and a basic group, e.g. amino, can also be present in the form of internal salts, i.e. in zwitterionic form, or a part of the molecule can be present as an internal salt, and another part as a normal salt.

The compounds, including their salts, can also be in the form of hydrates or solvates, or their crystals can include, e.g., the solvent used for crystallization.

The compounds of formula I and their salts, depending on the choice of the starting substances and working procedures, can be present in the form of one of the possible isomers, e.g. stereo-isomers or tautomers, or as a mixture thereof. In this context, pure isomers obtainable are, e.g., pure enantiomers, pure diastereoisomers or pure tautomers. Correspondingly, isomer mixtures which can be present are, e.g., racemates or diastereoisomer mixtures. Isomer mixtures of compounds of formula I, in free form or in salt form, can be separated into the components in a customary manner, e.g. on the basis of the physicochemical differences of the constituents, in a known manner by fractional crystallization, distillation and/or chromatography. Advantageously, the more active isomer is isolated.

Thus, one aspect of the invention is a therapeutic method for the treatment of biofilm formation in mammals. The method utilizes the class of iron chelators above-mentioned, which has been previously prepared and shown to be useful for the treatment of diseases which cause an excess of iron in the human or animal body or are caused by it, e.g. as mentioned in U.S. Pat. No. 6,596,750.

The preferred compound of formula I is Compound I of formula (I) is 4-[3,5-bis(2-hydroxyphenyl)-[1,2,4]triazol-1-yl]benzoic acid or a pharmaceutically acceptable salt. Pharmaceutical preparation comprising Compound I are disclosed, e.g. in the following International Patent Application WO2004/035026. Compound I can be administered according to the manufacturer's instructions.

The present invention relates to the use of a compound of formula I

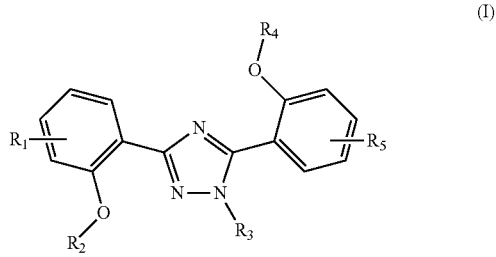

in which
R1 and R5 simultaneously or independently of one another are hydrogen, halogen, hydroxyl, lower alkyl, halolower alkyl, lower alkoxy, halo-lower alkoxy, carboxyl, carbamoyl, N-lower alkylcarbamoyl, N,N-di-lower alkylcarbamoyl or nitrile;

R2 and R4 simultaneously or independently of one another are hydrogen, unsubstituted or substituted lower alkanoyl or aroyl, or a radical which can be removed under physiological conditions;

R3 is hydrogen, lower alkyl, hydroxy-lower alkyl, halo-lower alkyl, carboxy-lower alkyl, lower alkoxycarbonyl-lower alkyl, R6R7N—C(O)-lower alkyl, unsubstituted or substituted aryl or aryl-lower alkyl, or unsubstituted or substituted heteroaryl or heteroaralkyl;

R6 and R7 simultaneously or independently of one another are hydrogen, lower alkyl, hydroxy-lower alkyl, alkoxylower alkyl, hydroxyalkoxy-lower alkyl, amino-lower alkyl, N-lower alkylamino-lower alkyl, N,N-di-lower alkylaminolower alkyl, N-(hydroxy-lower alkyl)amino-lower alkyl, N,N-di(hydroxy-lower alkyl)amino-lower alkyl or, together with the nitrogen atom to which they are bonded, form an azaalicyclic ring, preferably Compound I or a pharmaceutically acceptable salt thereof;

and wherein the prefix "lower" designates a radical having not more than 7 carbon atoms; e.g. 4-[3,5-bis(2-hydroxyphenyl)-[1,2,4]triazol-1-yl]benzoic acid; alternatively in combination with an antibiotic selected from the group consisting of aminoglycosides, e.g. gentamicin, amikacin, tobramycin; quinolones, e.g. ciprofloxacin, and levofloxacin; cephalosporins, e.g. ceftazidime, cefepime, cefpirome; ureidopenicillines such as piperacillin, ticarcillin; carbapenems, such as meropenem, imipenem; polymyxins such as polymyxin B, colistin and monobactams, such as for example aztreonam; e.g. in the form of a fixed combination;

(1) for the preparation of a medicament for the treatment of chronic *P. aeruginosa* infection,
(2) for the preparation of a medicament for the treatment of the biofilm formation,
(3) for the preparation of a medicament for the treatment of the biofilm formation of *P. aeruginosa*,
(4) for the preparation of a medicament for the treatment of the biofilm formation of *P. aeruginosa* in cystic fibrosis patients,
(5) for the preparation of a medicament for the prevention of the formation of biofilm of *P. aeruginosa*,
(6) for the preparation of a medicament for the prevention of the formation of biofilm of *P. aeruginosa* in cystic fibrosis patients,
(7) to reduce or eliminate the biofilms of *P. aeruginosa*,
(8) to impair the biofilm formation of, e.g. *P. aeruginosa*,
(9) to disrupt an established biofilm of, e.g. *P. aeruginosa*.

The present invention relates to a method of reducing and/or removing the biofilm formation on medical devices, e.g. catheters wherein Compound I is applied on said medical devices.

In another embodiment, the invention relates to the combination of Compound of formula I with an antibiotic which is active against *P. aeruginosa*. The present invention relates to said combination wherein the antibiotic is selected from the group consisting of aminoglycosides, e.g. gentamicin, amikacin, tobramycin; quinolones, e.g. ciprofloxacin, and levofloxacin; cephalosporins, e.g. ceftazidime, cefepime, cefpirome; ureidopenicillines such as piperacillin, ticarcillin; carbapenems, such as meropenem, imipenem; polymyxins such as polymyxin B, colistin and monobactams, such as for example aztreonam. Preferably, the antibiotic is gentamycin or tobramycin.

The present invention relates to a combination comprising (a) a compound of formula I as described above, preferably 4-[3,5-bis(2-hydroxyphenyl)-[1,2,4]triazol-1-yl]benzoic acid, or a pharmaceutically acceptable salt and (b) a antibiotic selected from the group consisting of aminoglycosides, quinolones, cephalosporins, ureidopenicillines, carbapenems, polymyxins and monobactams.

Any of the combination of components (a) and (b), the method of treating a warm-blooded animal comprising administering these two components, a pharmaceutical composition comprising these two components for simultaneous, separate or sequential use, the use of the combination for the delay of progression or the treatment or use as disclosed under (1) to (7) above or for the manufacture of a pharmaceutical preparation for these purposes or a commercial product comprising such a combination of components (a) and (b), all as mentioned or defined above, will be referred to subsequently also as COMBINATION OF THE INVENTION, i.e. so that this term refers to each of these embodiments which thus can replace this term where appropriate.

Simultaneous administration may, e.g., take place in the form of one fixed combination with two or more active ingredients, or by simultaneously administering two or more active ingredients that are formulated independently. Sequential use, e.g. administration, preferably means administration of one, or more, components of a combination at one time point, other components at a different time point, that is, in a chronically staggered manner, preferably such that the combination shows more efficiency than the single compounds administered independently, e.g. especially showing synergism. Separate use, e.g. administration, preferably means administration of the components of the combination independently of each other at different time points, preferably meaning that the components (a) and (b) are administered such that no overlap of measurable blood levels of both compounds are present in an overlapping manner, e.g. at the same time.

EXAMPLE 1

Material and Methods

Effect of on *P. aeruginosa* Growth

Growth with or without Compound I, e.g. at concentrations achieved in peripheral blood, under aerobic and anaerobic conditions with no added iron, 10, 30 and 50 $\mu$M iron. The median concentration of iron normally found in CF sputum is 30 $\mu$M. The effect of bacterial growth is determined using a standard method that involves inoculation of aliquots, e.g. 500 $\mu$l, of around $10^6$ bacteria in minimal media with succinate into borosilicate glass tubes, e.g. 12×75 mm, that are them incubated under aerobic and anaerobic conditions, e.g. at 37° C. Each experiment is undertaken in triplicate and each borosilicate tube is removed at regular intervals, e.g. 0, 4, 8, 12, 16, 20 and 24 hours and the optical density at 570 nm of the culture used as an indicator of the level of growth. Anaerobic culture conditions are generated using the Anaerogen™ (Oxoid) system. For anaerobic experiments, parallel cultures are set up so that cultures are not transiently exposed to oxygen, i.e. seven parallel cultures to allow sampling at the required times.

Effect of on *P. aeruginosa* Motility

The motility of *P. aeruginosa* will be monitored as described by Singh et al, Nature 2002, 417(6888):552-5, e.g. in the presence of additional iron. An increased and incoordinate motility correlates with the inability of *P. aeruginosa* to aggregate and initiate biofilm formation in vivo. The motility test are carried out in agar, e.g. swimming, swarming and twitching, e.g. with no added iron or 30 $\mu$M iron and then with or without Compound I, using established methods.

Effect of on *P. aeruginosa* Biofilms

For this purpose, two short-term biofilm models relevant for the early stages of biofilm formation are used: borosilicate tubes and cover-slip method.

In both models, the biofilm growth is studied with or without Compound I under either aerobic or anaerobic conditions and with or without added iron, i.e. 0, 10, 30 and 50 $\mu$M iron.

The anti-biofilm effects of Compound I are looked at according to the standard methods, i.e. optical density, confocal imaging software, e.g. COMSTAT program, to allow analysis of biofilm structure in a 3 dimensional perspective. The imaging system and use of BacLight LIVE/DEAD staining (Molecular Probes) in the cover-slip experiments allow to look at the effects on both bacterial microcolonies and biofilm structure.

Effect of *P. aeruginosa* Antibiotic Resistance

The minimal inhibitory concentrations (MICs) of the aminoglycosides gentamycin and tobramycin are determined under aerobic and anaerobic conditions in the presence of no added iron or 30 µM iron, with or without Compound I, e.g. and/or with varying concentrations of Compound I).

Effect of on *P. aeruginosa* Production of Virulence Factors

Production of several virulence factors can be induced by iron starvation. The potential of Compound I to induce bacterial virulence factor production in the presence or absence of Compound I will be determined as described Mow.

Effect on impairment of biofilm development by clinical *P. aeruginosa* strains isolated from the sputum of CF individuals, Effect on disruption established biofilms, Use of longer-term flow cell biofilm models with Compound I and antibiotics administered concurrently are studied.

LEGEND TO FIGURES

FIG. 1. Effect of Compound I on *P. aeruginosa* Growth and Biofilm Formation

Different concentrations of Compound I are assessed for their effect on aerobic and anaerobic (A) growth and (B) biofilm levels. Medium used is MMS supplemented with 0 or 10 µM FeCl3, as indicated (37° C., 24 h). Values shown represent the mean±SD of one representative experiment with 3 tubes per experiment.

Figure 2:
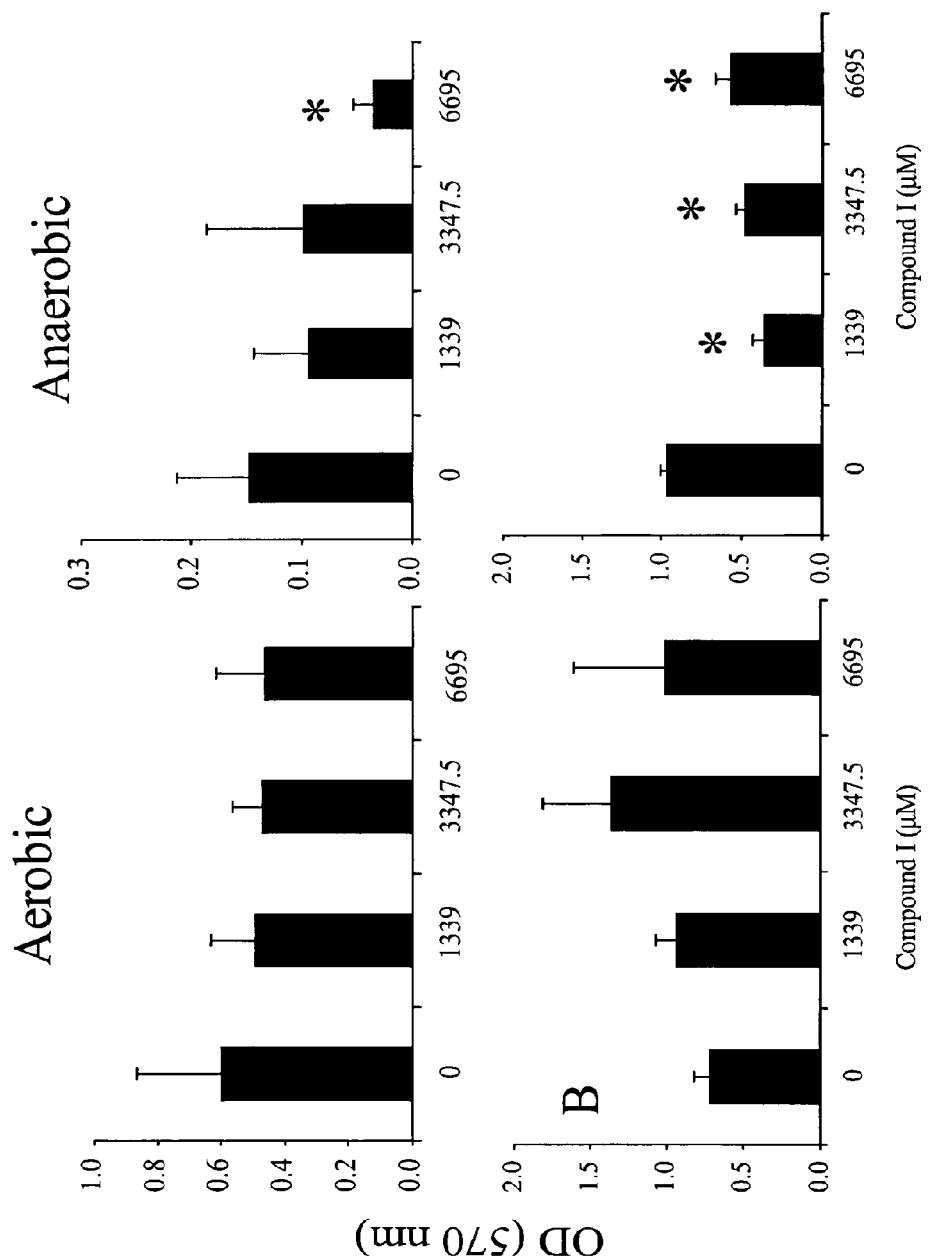

FIG. 2. Effect of High Concentrations of Compound I on *P. aeruginosa* Growth and Biofilm Formation Different concentrations of Compound I are assessed for their effect on aerobic and anaerobic (A) growth and (B) biofilm levels. Medium used is MMS supplemented with 10 µM FeCl3 (37° C., 24 h). Values shown represent the mean±SD of two experiments with 3 tubes per experiment. * Denotes significantly poorer levels in comparison to those seen when no chelator is present (P<0.05).

Figure 3:
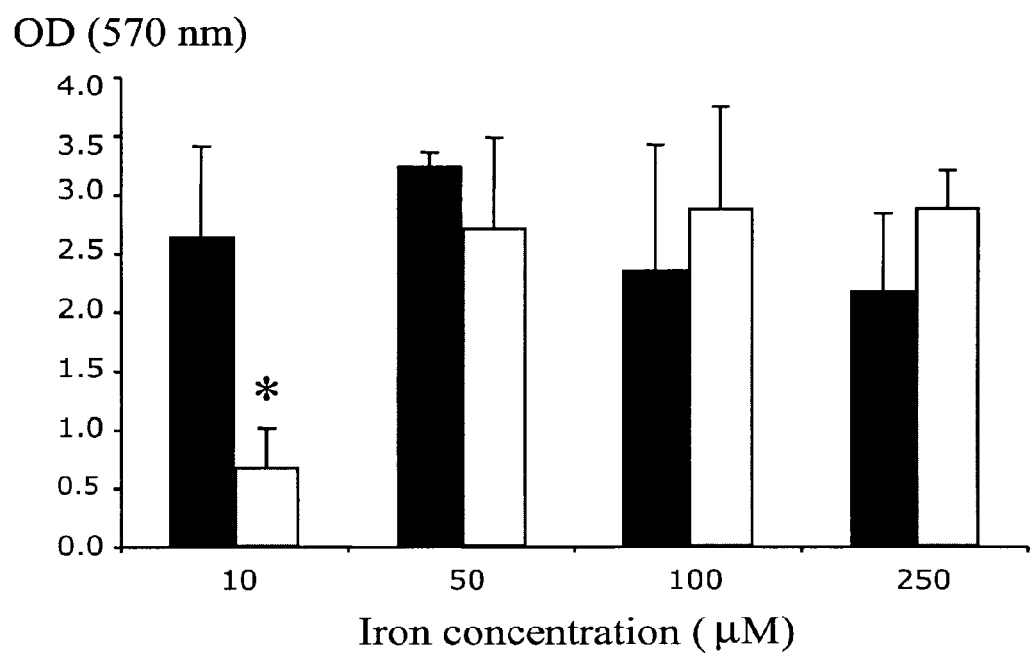

FIG. 3. Effect of Compound I on Anaerobic Biofilm Development in Different Iron Levels The effect of Compound I (1339 µM) on biofilm development in different iron concentrations, without Compound I (black columns) and with Compound I, 1339 µM (grey columns). Values shown represents the mean±SD of one representative experiment with 3 tubes per experiment. * denotes significantly poorer biofilms in comparison to biofilms at the same iron level without Compound I (P<0.05).

Figure 4:
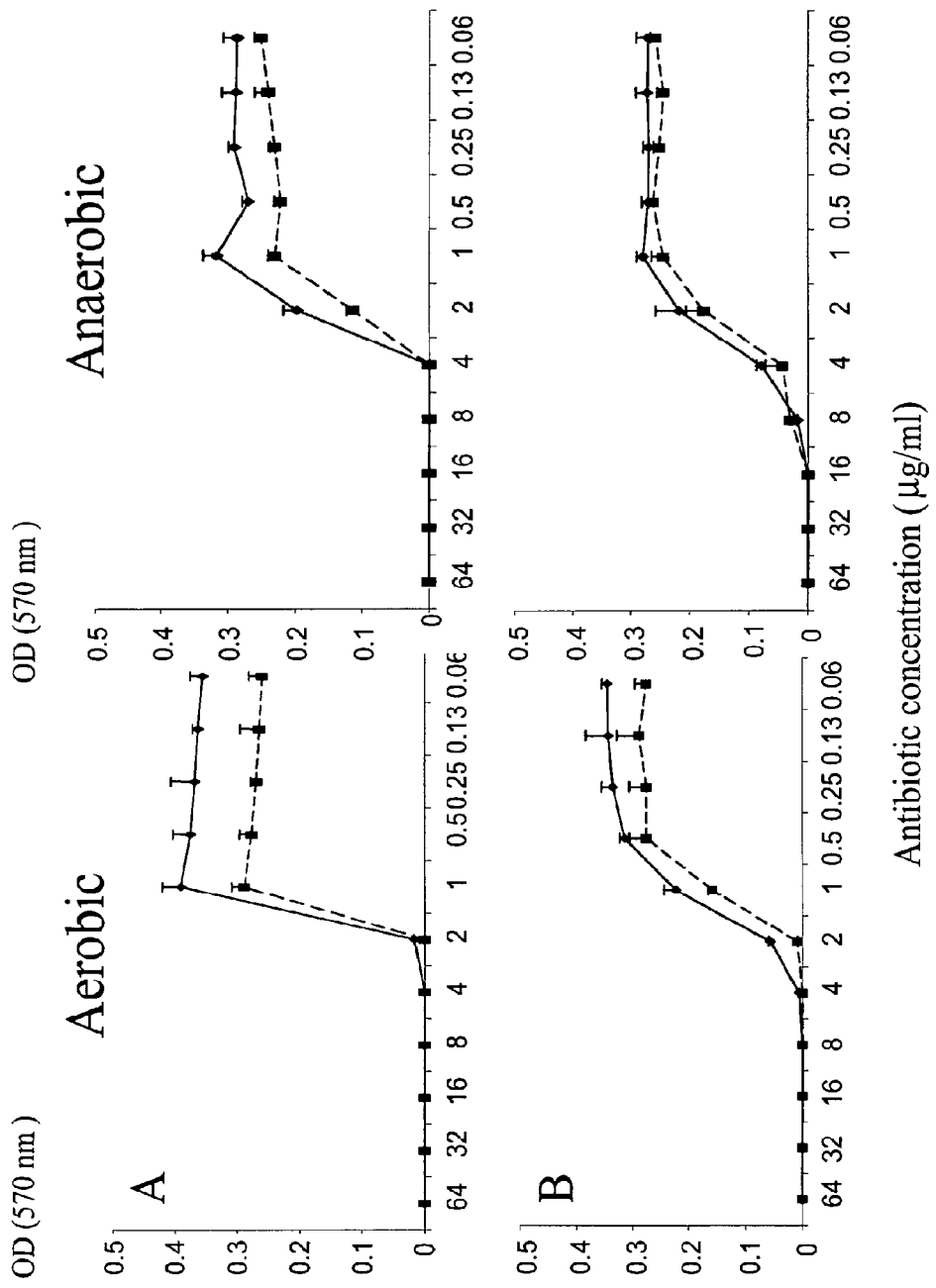

FIG. 4. Effect of Compound I on the MIC of (A) Colistin and (B) Tobramycin Against *P. aeruginosa* Strain PAO1

MICs are determined in MMS+10 uM FeCl3 supplemented with Compound I (1339 µM) (solid line) and without Compound I (dashed line). Values shown represent the mean±SD of a representative experiment with each condition tested in duplicate.

Figure 5:
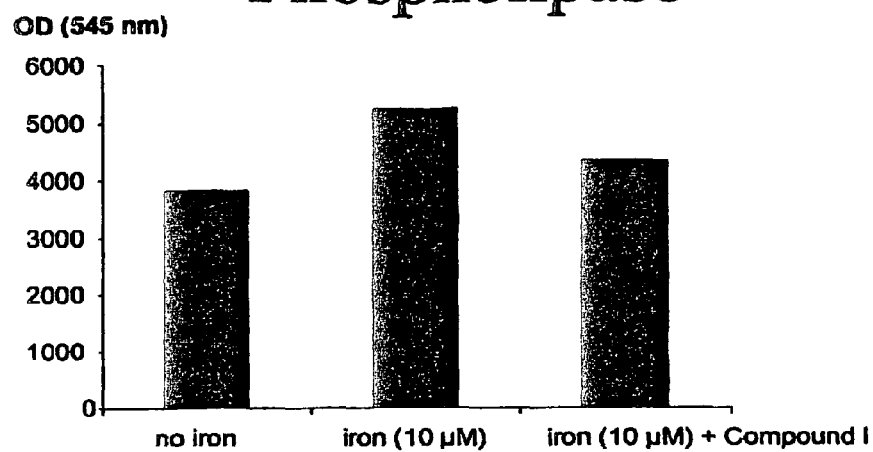
Figure 5:
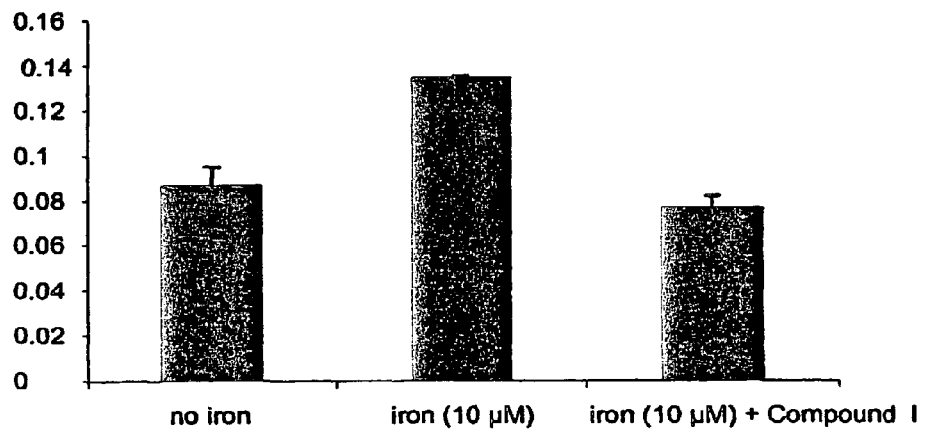

FIG. 5. Effect of Compound I on Phospholipase and Exotoxin A Production

Cultures are incubated under anaerobic conditions (24 h) with iron and Compound I (1339 µM) supplements as indicated (iron +ICL). Values shown represent the level of phospholipase lipase production (1 experiment) and the mean level±SD of exotoxin A production (1 experiment with each condition tested in duplicate).

RESULTS

1. The Effects of Compound I on Growth and Biofilm Development

The effects of Compound I on planktonic growth and biofilm development re assessed in the short-term borosilicate glass tube biofilm model. In this model, a biofilm is grown on a glass surface, and this is subsequently stained and solubilized. The optical density (OD: 570 nm) of the solution corresponds with the level of biofilm development.

Using this model, bacterial growth and biofilm levels are determined after incubation (24 h, 37° C.) in minimal medium supplemented with succinate (MMS)+10 µM FeCl3 (aerobic and anaerobic atmospheres). The low solubility of Compound I in MMS medium (pH 7.0) means that initial experiments are necessarily conducted at low chelator concentrations of 0-100 µM. At these low concentrations, Compound I does not impair aerobic or anaerobic growth or biofilm development (FIG. 1).

Compound I is dissolved in the surfactant PEG 400 and then diluted it in MMS medium to achieve a concentration of up to 6695 µM of Compound I. In separate experiments, it is shown that surfactant alone did not affect growth or biofilm levels (data not shown). The higher concentration of Compound I is able to significantly impair *P. aeruginosa* growth and biofilm levels under anaerobic conditions (P<0.05), but not under aerobic conditions. It is investigated whether Compound I is impairing anaerobic biofilm development by directly reducing the level of iron in the medium, or whether it is acting by an iron-independent mechanism. Compound I at a concentration of 1339 µM is tested to see if it continued to impair anaerobic biofilm development as the concentration of iron is increased in the culture medium. As the iron levels increased, Compound I becomes less effective, suggesting that its main effect is mediated through iron chelation and that this biofilm inhibition can be overcome by high iron levels that presumably saturate Compound I's binding capacity.

2. Compound I Enhances the Sensitivity of *P. aeruginosa* to Antibiotics.

The mean inhibitory concentrations (MICS) of two antibiotics commonly used antibiotics to treat CF individuals, tobramycin and colistin, are tested against *P. aeruginosa*. This is done in MMS+10 µM FeCl3 with and without Compound I (1339 µM) under aerobic and anaerobic atmospheres (FIG. 4). The presence of Compound I does not alter the MIC.

3. Compound I Influences the Production of Virulence Factors

Virulence factors examined to date are phospholipase C and exotoxin A (ETA). The production of these factors under anaerobic conditions is examined after incubation in a) MMS medium alone, b) MMS medium supplemented with 10 µM FeCl3 and finally, c) MMS medium alone supplemented with both 10 µM FeCl3 and Compound I (1339 µM). In the presence of supplemental iron there is an increased level of both virulence factors in comparison to that seen in same medium without iron. This increase is negated when Compound I is added suggesting Compound I can interfere with iron-related virulence factor production by *P. aeruginosa* (FIG. 5).

It is demonstrated therapeutic potential for Compound I directed against *P. aeruginosa* under the sort of environmental conditions encountered in the CF lung, i.e. low oxygen tensions and available iron.

1. Compound I significantly impairs P. aeruginosa growth and biofilm development under anaerobic conditions. This appears to be directly related to Compound I reducing the level of iron available to P. aeruginosa.
2. Compound I does not alter the MIC of the antibiotics tobramycin and colistin when tested against planktonic organisms.
3. Compound I does not stimulate phospholipase C or ETA production, but in contrast, it reduces the production of these bacterial virulence factors in the presence of iron.

The invention claimed is:

1. A combination comprising 4-[3,5-bis(2-hydroxyphenyl)-[1,2,4]triazol-1-yl]benzoic acid or a pharmaceutically acceptable salt thereof and tobramycin.

2. The combination of claim 1, wherein the combination is a fixed dose combination.

3. A method of treating or preventing P. aeruginosa infection in a patient by administering to the patient 4-[3,5-bis(2-hydroxyphenyl)-[1,2,4]triazol-1-yl]benzoic acid or a pharmaceutically acceptable salt thereof.

4. The method of claim 3 wherein the P. aeruginosa infection is chronic.

5. The method of claim 3 wherein P. aeruginosa forms a biofilm.

6. The method of claim 5 wherein the treatment comprises preventing biofilm formation.

7. The method of claim 3 wherein the patient is a cystic fibrosis patient.

8. A method of treating P. aeruginosa infection in a patient by administering to the patient a combination comprising an aminoglycoside antibiotic and the compound of formula I

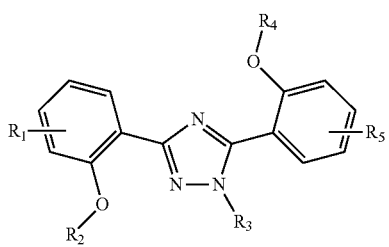

(I)

in which

R1 and R5 simultaneously or independently of one another are hydrogen, halogen, hydroxyl, lower alkyl, halolower alkyl, lower alkoxy, halo-lower alkoxy, carboxyl, carbamoyl, N-lower alkylcarbamoyl, N,N-di-lower alkylcarbamoyl or nitrile;

R2 and R4 simultaneously or independently of one another are hydrogen, unsubstituted or substituted lower alkanoyl or aroyl, or a radical which can be removed under physiological conditions;

R3 is hydrogen, lower alkyl, hydroxy-lower alkyl, halolower alkyl, carboxy-lower alkyl, lower alkoxycarbonyl-lower alkyl, R6R7N—C(O)-lower alkyl, unsubstituted or substituted aryl or aryl-lower alkyl, or unsubstituted or substituted heteroaryl or heteroaralkyl;

R6 and R7 simultaneously or independently of one another are hydrogen, lower alkyl, hydroxy-lower alkyl, alkoxy-lower alkyl, hydroxyalkoxy-lower alkyl, amino-lower alkyl, N-lower alkylamino-lower alkyl, N,N-di-lower alkylaminolower alkyl, N-(hydroxy-lower alkyl)amino-lower alkyl, N,N-di(hydroxy-lower alkyl)amino-lower alkyl or, together with the nitrogen atom to which they are bonded, form an azaalicyclic ring;

and wherein the prefix "lower" designates a radical having not more than 7 carbon atoms.

9. The method of claim 8 wherein the P. aeruginosa infection is chronic.

10. The method of claim 8 wherein P. aeruginosa forms a biofilm.

11. The method of claim 10 wherein the treatment comprises preventing biofilm formation.

12. The method of claim 8 wherein the patient is a cystic fibrosis patient.

13. The method of claim 8 wherein the compound of formula I is 4-[3,5-bis(2-hydroxyphenyl)-[1,2,4]triazol-1-yl]benzoic acid or a pharmaceutically acceptable salt thereof.

14. The method of claim 8 wherein the aminoglycoside antibiotic is tobramycin or gentamycin.

15. The method of claim 14 wherein the aminoglycoside antibiotic is tobramycin.

16. The method of claim 8 wherein the combination is a fixed dose combination.

\* \* \* \* \*